United States Patent [19]

Djabbarah et al.

[11] Patent Number: 5,470,749
[45] Date of Patent: Nov. 28, 1995

[54] METHOD FOR DETERMINING STEAM QUALITY USING A FOAMING SURFACTANT

[75] Inventors: Nizar F. Djabbarah, Richardson; Eve S. Sprunt, Farmers Branch, both of Tex.

[73] Assignee: Mobil Oil Corporation, Fairfax, Va.

[21] Appl. No.: 112,292

[22] Filed: Aug. 27, 1993

[51] Int. Cl.$^6$ ................................................. G01N 33/00
[52] U.S. Cl. .................... 436/38; 73/64.44; 166/250.06; 166/272; 436/25; 436/27; 436/28; 436/30; 436/32
[58] Field of Search ..................... 166/250, 272; 73/64.44; 436/38, 27, 25, 28, 29, 30, 32, 39

[56] References Cited

U.S. PATENT DOCUMENTS

| | | | |
|---|---|---|---|
| 3,276,460 | 10/1966 | Feld | 73/64.44 X |
| 3,430,483 | 3/1969 | Clawson et al. | 73/64.44 X |
| 3,686,924 | 8/1972 | Ludt et al. | 73/64.44 |
| 4,086,964 | 5/1978 | Dilgren et al. | 166/272 |
| 4,137,462 | 1/1979 | Wyler | 250/573 |
| 4,148,217 | 4/1979 | Engle | 73/60.1 |
| 4,193,290 | 3/1980 | Sustek et al. | 73/29 |
| 4,393,937 | 7/1983 | Dilgren et al. | 166/272 |
| 4,532,993 | 8/1985 | Dilgren et al. | 166/303 |
| 4,547,078 | 10/1985 | Long et al. | 374/42 |
| 4,562,727 | 1/1986 | Dilgren et al. | 73/60.1 |
| 4,570,711 | 2/1986 | Falls et al. | 166/272 |
| 4,763,730 | 8/1988 | Suzuki | 166/273 |
| 5,000,262 | 3/1991 | Danzik | 166/272 |
| 5,000,263 | 3/1991 | Stowe | 166/303 |
| 5,042,583 | 8/1991 | D'Souza et al. | 166/272 |
| 5,094,103 | 3/1992 | Wicks et al. | 73/155 |
| 5,138,876 | 8/1992 | Moore et al. | 73/155 |
| 5,193,618 | 3/1993 | Loh et al. | 166/272 |
| 5,234,054 | 8/1993 | Chou | 166/272 |
| 5,273,682 | 12/1993 | Danzik | 252/320 |

OTHER PUBLICATIONS

S. H. Raza & S. S. Marsden, "The Streaming Potential and the Rheology of Foam", Society of Petroleum Eng. Journal, 1967, pp. 359–368.

S. H. Raza & S. S. Marsden, "The Flow of Foam: Rheology and Streaming Potential", SPE No. 1205, 40th Annual Fall Meeting of the Society of Petroleum Engineers, Denver, Colo. Oct. 3–6, 1965.

*Primary Examiner*—James C. Housel
*Assistant Examiner*—Harold Y. Pyon
*Attorney, Agent, or Firm*—Alexander J. McKillop; Lawrence O. Miller

[57] ABSTRACT

Steam quality is measured by mixing the steam with a small amount of surfactant to convert the steam to a stable foam, passing the stable foam through a capillary tube to determine foam quality (volume of vapor per volume of vapor and liquid) by measuring the streaming potential coupling coefficient of the foam passing through the tube, and converting foam quality (volume per volume) to steam quality (mass of vapor per mass of vapor and liquid) based upon the fluid density of the liquid-water and water-vapor phase of the steam.

6 Claims, 1 Drawing Sheet

METHOD FOR DETERMINING STEAM QUALITY USING A FOAMING SURFACTANT

FIELD OF THE INVENTION

The present invention pertains to a method for measuring steam quality. It is particularly applicable to steam that is being injected into wells for enhanced oil recovery.

BACKGROUND OF THE INVENTION

There are many current methods for measuring the quality of steam such as calorimetry, laser-beam density measurements and flow measurements (orifice, venturimeters and nozzles).

There are different types of calorimetry such as throttling, separating throttling, condensing, or superheating calorimetry. Aside from sampling inaccuracy, calorimeters are manpower intensive and do not lend themselves to remote sensing. An additional problem associated with a throttling calorimeter is that its applicability is limited to higher ranges of steam quality (>90%). The flow measurements (orifices, venturimeters and nozzles) require frequent maintenance, or else they become inaccurate. Examples of such prior arrangements are the following U.S. Patent Nos.: Hagnes, Jr. et al. U.S. Pat. No. 3,499,488, issued Mar. 10, 1970; Wyler U.S. Pat. No. 4,137,462, issued Jan. 30, 1979 and Susteh et al. U.S. Pat. No. 4,193,290 issued Mar. 18, 1980.

The present invention provides a reliable continuous method and system to measure steam quality without necessitating a total separation of the liquid and vapor phase thereof.

SUMMARY OF THE INVENTION

This invention provides a method for continuously measuring the quality of steam supplied to an injection well or the like, comprising withdrawing a sample of the steam and mixing it with a small amount of surfactant to convert the steam to stable foam. Thereafter, the quality of foam is determined by measuring the streaming potential coupling coefficient of the foam and then converting foam quality (volume of vapor per volume of vapor and liquid) to steam quality (mass of vapor per mass of vapor and liquid) using fluid densities of the liquid water and water vapor at the measured temperature and pressure. Suitable surfactants include linear toluene sulfonates, alpha olefin sulfonates, and dimers of alpha olefin sulfonates.

The invention also provides a steam quality monitoring system for use with steam injection wells or the like. It comprises a conduit for delivering steam to the injector well, and a line branched from the main steam line to withdraw a sample of the steam by means of a sampling time release valve. The steam is mixed with a small amount of surfactant in a static mixer to form a stable foam. The stable foam is fed into an electrically non-conductive tube provided with means for measuring the voltage drop in the foam across a selected length of the tube and means for measuring the pressure drop in the foam across a selected length of the tube to indicate the streaming potential coupling coefficient in volts per psi. Means are provided to measure the temperature and pressure of the foam in the tube to determine the fluid density of the liquid-water and water-vapor in the foam. In another embodiment, a static mixer is placed in the main steam line before the steam sampling line to avoid gravity segregation of the liquid water and water vapor in the main steam line.

DESCRIPTION OF THE PREFERRED EMBODIMENTS

Determination of the quality of steam is an important aspect of steam injection in thermal recovery operations for petroleum wells, and the like. In addition, it is important to determine the steam quality of steam generated in the chemical process industries and nuclear power steam generators. The present invention provides a method and system for measuring steam quality that can be used in-line or in a sampling vessel to determine the quality of steam from a boiler. The method of the present invention lends itself to remote sensing and is not maintenance intensive.

The steam quality of course is the degree of dryness of the steam. Dry steam, as is known to those skilled in the art, is steam which is 100% water vapor with no liquid water. This steam is designated as one-phase steam. Two-phase steam is synonymous with wet steam. Wet steam is water vapor with liquid water. The amount of water vapor in wet steam is indicative of steam quality. Steam quality is an important parameter in determining the efficiency of the steam generator. Also of greater importance is the effectiveness of a steam flood in a steam injection operation for enhanced oil recovery, i.e., where steam is injected into a viscous oil-containing formation by means of an injection well and oil is recovered from the formation from a spaced-apart production well. The injected steam heats the oil thereby reducing its viscosity which improves oil mobility and enhances its recovery. The steam being injected into the formation is saturated, which simply means that there is present both a liquid phase and a gaseous phase simultaneously at the point of injection. Ordinarily saturated steam is defined in terms of quality by specifying the weight fraction of the vapor phase. Thus, 80 percent quality steam means that 80 percent of the steam on the basis of weight is vapor with the remaining 20 percent being liquid phase. It is generally satisfactory to use steam in the quality range from about 40 to 100 percent. It is therefore important to know the quality of the steam in order to determine the effectiveness of the steam flood.

In order to continuously monitor the quality of steam in-line being supplied to an injection well, and to do so adjacent to the well itself, a system according to this invention may be employed. Such a system is schematically illustrated in FIG. 1 adjacent a steam pipeline.

Figure 1:
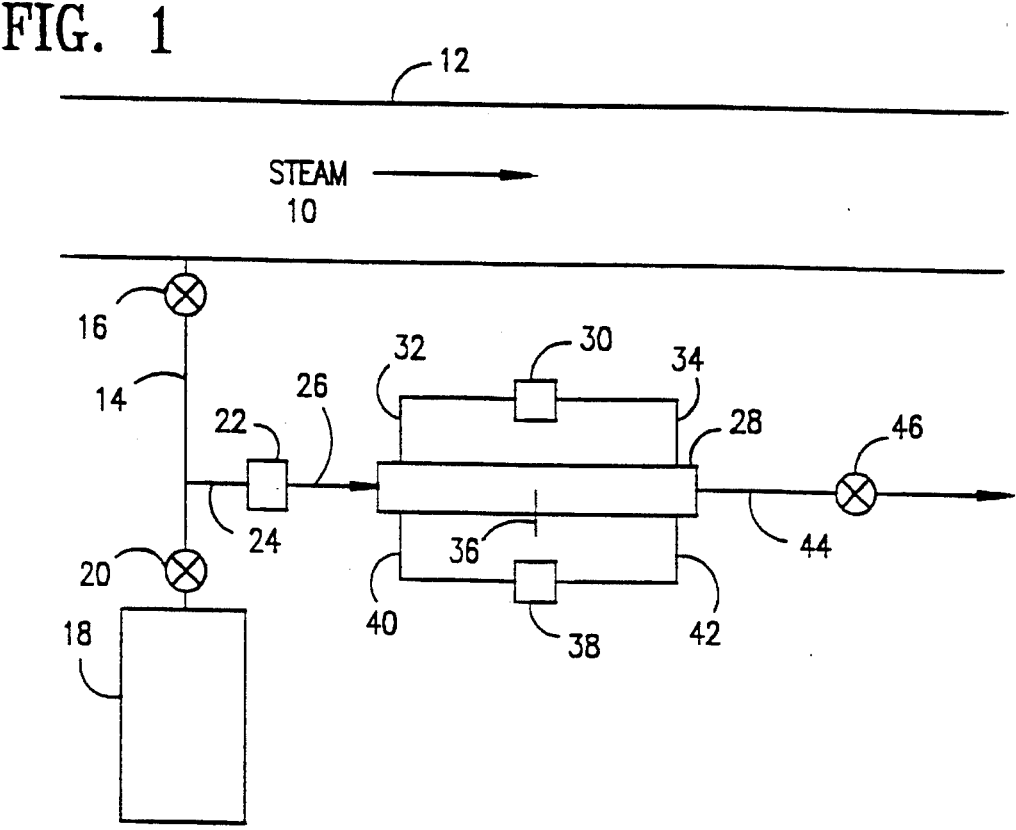
FIG. 1 is a schematic illustrating the elements of a steam quality monitoring system according to the invention.

Referring to FIG. 1, steam 10 flows through a steam line or pipe 12 from a conventional steam generator (not shown) to an injector well (not shown). A sample of the steam 10 is withdrawn from line 12 into sampling line 14 by means of a sampling time release valve 16. As an option, a static mixer (not shown) may be placed in line 12 before the sampling line 14 to avoid gravity segregation of the liquid water and water vapor in the steam 10. This enables a more representative sample of the steam quality. A surfactant supply container 18 is connected to the sampling line 14 by means of a time-release control valve 20 which is used to inject the required amount of surfactant into line 14. The steam and the surfactant are then fed into a static mixer 22 through line 24 where the steam and surfactant are mixed to form a stable foam. The static mixer 22 is used to provide the medium for mixing the surfactant and steam. A suitable static mixer 22 is manufactured by Kay Ray Inc., under the trade name Brenner two-phase mixer. The amount of surfactant injected into the steam is sufficient to create a stable foam but is so small, preferably not more than about 1% by weight of the liquid phase of the steam, that it does not have a measurable effect on the volume. Therefore, the volume of foam is equal to the volume of steam. The duration of surfactant injection should be sufficient to produce foam in sampling line 14 for about five (5) minutes. Foam then flows through line 26 into an electrically shielded capillary tube 28 having an inner surface that is non-conductive electrically. The inlet-outlet pressure drop across the capillary tube 28 is measured by means of pressure transducer 30 connected to the capillary tube at location 32 and 34. The temperature of the foam in the capillary tube 28 is measured by means of thermocouple 36 and a direct current (DC) voltmeter 38 is used to measure the voltage drop between electrodes 40 and 42 which corresponds to the streaming potential, $\Delta E$. The streaming potential coupling coefficient is the streaming potential ($\Delta E$) in volts divided by the inlet-outlet pressure drop across the capillary tube 28 in pounds per square inch. Foam is removed from the capillary tube 28 through line 44 and the outlet pressure is maintained near the steam pressure in line 12 by means of a pressure release valve 46. The whole assembly is thermally insulated to maintain steamline temperature. A glass-bead packed tube with an electrically non-conductive and electrically shielded inner surface may be used instead of the capillary tube 24.

Self potential in foams is mentioned in an article entitled "The Streaming Potential and The Rheology of Foam" that was authored by S. H. Raza and S. S. Marsden in the Society of Petroleum Engineering Journal, (1967), pages 359–368. An experimental and theoretical study of streaming potential generated during a flow of foam resulted in several conclusions. First, the streaming potential was directly proportional to the pressure differential applied across a flow system and to a radius of the flow channel. Second, the streaming potential of foam is greatly dependent upon the quality of foam; and the higher the quality, the greater the streaming potential. Third, the foams generated from ionic surfactants produce lower streaming potentials than those from nonionic surfactants. This article is hereby incorporated herein by reference.

Figure 2:
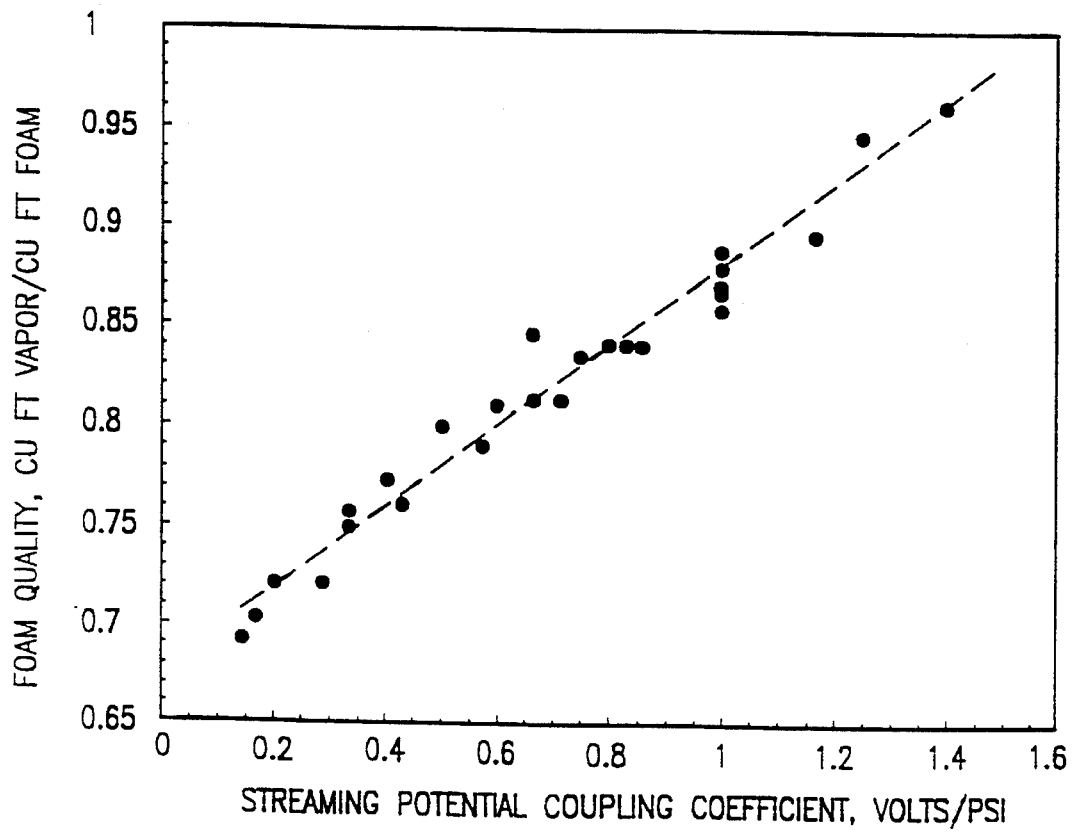
FIG. 2 is a graph illustrating the relationship of steaming potential coupling coefficient, in volts/psi, to foam quality, in cu. ft. vapor/cu. ft. foam.

FIG. 2 is a plot of the relationship between steam foam quality (cubic feet of vapor per cubic feet of foam) and the streaming potential coupling coefficient (volts/psi) based upon measurements made by S. H. Raza and S. S. Marsden as described in their article entitled, "The Flow of Foam: Rheology and Streaming Potential", SPE No. 1205, Presented at the 40th Annual Fall Meeting of the Society of Petroleum Engineers, Denver, Colo., Oct. 3–6, 1965. This article is hereby incorporated by reference. Based upon the results shown in FIG. 2, Raza and Marsden derived the following equation:

$$\frac{\Delta E}{\Delta P} = \frac{D\zeta}{4\pi\kappa\mu} \left\{ \frac{1}{1-\left(\tau-\frac{1}{\tau}\right)-\frac{\phi}{\tau}} \right\}$$

where, $\Delta E$=streaming potential, volts $\Delta P$=pressure drop, psi

D=dielectric constant $\zeta$=zeta potential, volts

K=consistency index, poise $\mu$=foam effective viscosity, poise $\tau$=electrical tortuosity, dimensionless $\phi$=foam quality, volume of gas/volume of foam The choice of the surfactant is dictated by two factors: chemical stability and ability to produce stable foam at steam injection temperature (500° F.) and pressure (680 psi). Linear toluene sulfonates, coconut alkanolamides, alpha-olefin sulfonates, modified ether sulfate esters, and dimers of alpha-olefin sulfonates are some surfactants which meet the above high temperature requirements. For measuring the relative amount of a gas in a low temperature application such as a gas-liquid two phase flow system, suitable surfactants include ethoxylated sulfated alcohols, polypropylene EO polyols, polyethylene glycol ether of linear alcohols, octyphenyl nonylethoxy alcohol, alkanolamides, coconut alkanolamides, and modified ether sulfate esters. The preferred surfactants for low temperature use would be ethoxylated sulfated alcohols and/or octyphenyl nonylethoxy alcohol. The preferred surfactants for high temperature use would be dimers of alpha olefin sulfonates and linear toluene sulfonates. Table 1, lists examples of commercial names and vendors of each type of surfactant.

TABLE 1

| Trade Name | Type | Vendor |
| --- | --- | --- |
| Alipal CD-128 | Ethoxylated sulfated alcohol | GAF |
| Chaser SD 1000 | Alpha-olefin sulfonate dimer | Chevron Chemical Co. |
| Chaser SD 1020 | Linear toluene sulfonate | Chevron Chemical Co. |
| Monamid 150AD | Coconut alkanolamide | Mona |
| Plurafac Series | Modified ether sulfate ester | BASF |
| Pluronic Series | Polpropylene EO polyols | BASF |
| Tergitol Series | Polyethylene glycol ether of linear alcohols | Union Carbide |
| Triton Series | Octyphenyl nonylethoxy alcohol | Rohm and Haas |
| Witcamide Series | Alkanolamide | Witco |

An example of applying this invention to determine the quality of steam being delivered to an injector well in a steamflood oil recovery operation would typically involve the flow of about 20 gallons per minute, cold water equivalent, in a 2 inch diameter pipe 12. At a predetermined time, the sampling valve 16 injects steam 10 into the sampling line 14 to clean the line. After the line is cleaned (2–5 minutes later) the surfactant valve 20 is activated to inject a pulse of Triton X-100 surfactant for 5 minutes. The surfactant is mixed with the steam in the static mixer 22 where foam is generated. Steam-vapor makes up the gaseous (dispersed) component of the foam while the steam liquid makes up the liquid component of the foam. As the foam enters and leaves the electrically non-conductive and electrically shielded portion of the capillary tube 28, its temperature, upstream and downstream pressure, and the DC voltage drop are measured and recorded.

If the upstream and downstream pressures are 680 and 660 psi, respectively, the temperature is 500° F., and the streaming potential is 29 volts, then the coupling coefficient streaming potential is 1.45 [29/(680–660)] volts/psi. Referring to FIG. 2, the corresponding foam quality is 97% (i.e. 97 Cu. Ft. water vapor per 100 Cu. Ft. steam). At the above conditions the specific volume of liquid-water and water-vapor are 0.02043 Cu. Ft./lb. and 0.6761 Cu. Ft./lb, respectively. Converting foam quality (volume of vapor per volume of vapor and liquid) to steam quality (mass of vapor per mass of vapor and liquid) using these densities, the corresponding steam quality is 49.42 pounds of water vapor per 100 pounds of steam.

In another embodiment, the capillary tube 28 may be calibrated by passing foams of differing known quality (volume of vapor per volume of vapor and liquid) through the capillary tube 28 and measuring the streaming potential coupling coefficient (volts/psi) for each foam. Then, if you plot foam quality (volume vapor per volume of vapor and liquid) against the streaming potential coupling coefficient (volts/psi), the results would be similar to the results shown in FIG. 2 obtained from measurements made by S. H. Raza and S. S. Marsden as described above. These results would then enable you to determine the foam quality (volume of vapor per volume of vapor and liquid) of a sample of foam being tested of unknown quality by passing it through the capillary tube and measuring its streaming potential coupling coefficient.

Application of the present invention is not limited to thermal oil recovery processes but may be used to determine quality of steam in any process that involves steam such as steam boilers in the nuclear power generation industry.

Application of the present invention is also not limited to steam. It may be used to determine the relative amounts of gas and liquid in any process that involves the multiphase flow of gas and slightly electrically conductive or nonconductive liquids such as organic solvents and hydrocarbons. In that case the thermal stability requirement of the surfactant may be relaxed or restricted to include surfactants that produce stable foam at higher or lower temperatures, depending on the temperature and pressure of the process under consideration.

In addition, the sampling and measurement process of the present invention may be conducted manually or may be automated and programmed to be done at predetermined intervals, with results telemetered to a remote site.

Obviously, many other variations and modifications of this invention as previously set forth may be made without departing from the spirit and scope of this invention as those skilled in the art readily understand.

What is claimed is:

1. A method for continuously measuring the quality of a flowing stream of steam at pressure and temperature substantially above atmospheric pressure and room temperature comprising:

a) mixing steam of a known quality (volume of vapor per volume of vapor and liquid) with a surfactant not greater than about 1% by weight of the liquid phase of the steam to form a stable foam having a quality (volume of vapor per volume of vapor and liquid) equal to the steam quality (volume of vapor per volume of vapor and liquid);

b) passing the stable foam from step a) through an electrically non-conductive shielded capillary tube and measuring the voltage drop between two electrodes spaced across a selected length of the tube and the pressure drop across the same selected length of the tube;

c) repeating steps a) and b) using steam of different qualities;

d) plotting the relationship between the ratio of voltage drop and pressure drop versus the foam quality (volume of vapor per volume of vapor and liquid) for each sample of steam tested in steps a) and b);

e) withdrawing successive a samples of the flowing stream of steam of unknown quality and repeating steps a) and b) for each sample to determine the ratio of voltage drop and pressure drop of the stable foam formed from said steam and measuring the temperature of the stable foam formed from said steam to determine the specific volume of the liquid-water and water-vapor phase of the steam forming the stable foam;

f) determining the foam quality (volume/volume) of each sample of the stable foam in step e) graphically from the relationship between foam quality (volume/volume) and the ratio of voltage drop and pressure drop plotted in step d) which equals steam quality; and g) converting the steam quality (volume of vapor per volume of foam) obtained in step f) for each sample to steam quality (mass of vapor per mass of vapor and liquid) using the specific volume of the liquid-water and water-vapor phase of the steam determined in step e).

2. The method as recited in claim 1 wherein the surfactant is selected from the group consisting of linear toluene sulfonates, alpha-olefin sulfonates, dimers of alpha-olefin sulfonates, coconut alkanolamides and modified ether sulfate esters.

3. The method as recited in claim 1 wherein the voltage drop and pressure drop are measured across the inlet and outlet of the capillary tube.

4. A method for continuously measuring the amount of gas and liquid in a two phase flow mixture of gas and liquid at pressure and temperature substantially above atmospheric pressure and room temperature comprising:

a) mixing a gas/liquid mixture of a known quality (volume of gas per volume of gas and liquid) with a surfactant not greater than about 1% by weight of the liquid phase of the steam to form a stable foam having a quality (volume of gas per volume of gas and liquid) equal to the gas/liquid quality (volume of gas per volume of gas and liquid);

b) passing the stable foam of known quality through an electrically non-conductive shielded capillary tube and measuring the voltage drop ($\Delta E$) between two electrodes across a selected length of the tube and pressure drop ($\Delta P$) across the same selected length of the tube;

c) repeating steps (a) and (b) using a gas/liquid mixture of different qualities;

d) plotting the relationship between the ratio of voltage drop and pressure drop versus the quality of the stable gas/liquid mixtures tested in steps a) and b);

e) withdrawing, successive samples of the gas/liquid flow mixture of unknown quality and repeating steps a) and b) for each sample to determine the ratio of voltage drop and pressure drop of the stable foam of unknown quality and measuring the temperature of said stable foam to determine the specific volume of the liquid-water and water-vapor phase of the gas/liquid mixture forming said stable foam;

f) determining the foam quality (volume/volume) of each sample of the stable foam in step e) graphically from the relationship between foam quality (volume/volume) and the ratio of voltage drop and pressure drop plotted in step (d) which equals gas/liquid quality; and g) converting the gas/liquid quality (volume of gas per volume of gas and liquid) obtained in step f) for each sample to gas/liquid quality (mass of gas per mass of gas and liquid) using the specific volume of the gas/liquid mixture determined in step e).

5. The method as recited in claim 4 wherein the surfactant is selected from the group consisting of ethoxylated sulfated alcohols, polypropylene EO polyols, polyethylene glycol ether of linear alcohols, octyphenyl nonylethoxy alcohol, alkanolamides and modified ether sulfate esters.

6. The method as recited in claim 4 wherein the voltage drop and pressure drop are measured across the inlet and outlet of the capillary tube.

* * * * *